(12) United States Patent
Lee et al.

(10) Patent No.: US 9,863,908 B2
(45) Date of Patent: Jan. 9, 2018

(54) LOW DRIFT ION SELECTIVE ELECTRODE SENSORS

(71) Applicant: BioChem Technology, Inc., King of Prussia, PA (US)

(72) Inventors: George Jaw Fang Lee, Berwyn, PA (US); Sergey K. Maneshin, Upper Holland, PA (US); Steven Kestel, Norristown, PA (US)

(73) Assignee: BioChem Technology, Inc., King of Prussia, PA (US)

( * ) Notice: Subject to any disclaimer, the term of this patent is extended or adjusted under 35 U.S.C. 154(b) by 59 days.

(21) Appl. No.: 14/787,879

(22) PCT Filed: Apr. 10, 2014

(86) PCT No.: PCT/US2014/033584
§ 371 (c)(1),
(2) Date: Oct. 29, 2015

(87) PCT Pub. No.: WO2014/179011
PCT Pub. Date: Nov. 6, 2014

(65) Prior Publication Data
US 2016/0109402 A1    Apr. 21, 2016

Related U.S. Application Data

(60) Provisional application No. 61/818,491, filed on May 2, 2013.

(51) Int. Cl.
*G01N 27/333*    (2006.01)
*G01N 27/30*    (2006.01)

(52) U.S. Cl.
CPC ....... *G01N 27/3335* (2013.01); *G01N 27/301* (2013.01)

(58) Field of Classification Search
CPC . G01N 27/3335; G01N 27/301; G01N 27/401
See application file for complete search history.

(56) References Cited

U.S. PATENT DOCUMENTS

| 3,450,631 A | 6/1969 | Bloch et al. |
| 3,706,649 A | 12/1972 | Cosgrove et al. |
| 4,214,968 A | 7/1980 | Battaglia et al. |

(Continued)

FOREIGN PATENT DOCUMENTS

| GB | 1 437 091 | 5/1976 |
| JP | 61-88134 | 5/1986 |
| WO | 2008/076491 | 6/2008 |

OTHER PUBLICATIONS

Stauthamer, W. P. R. V. et al., "Influence of Plasticizer on the Selectivity of Nitrate-Sensitive CHEMFETs," *Sensors and Actuators B*, Feb. 1, 1994, vol. 17, No. 3, pp. 197-201.

(Continued)

*Primary Examiner* — J. Christopher Ball
(74) *Attorney, Agent, or Firm* — DLA Piper LLP (US)

(57) ABSTRACT

An ion selective electrode sensor includes a housing containing an internal solution and enclosing a reference element containing a metal salt solution; open mesh fabric sieves traversing an opening in the housing; and at least one ion sensitive film layer on the mesh fabric sieves.

15 Claims, 2 Drawing Sheets

(56) References Cited

U.S. PATENT DOCUMENTS

| | | | |
|---|---|---|---|
| 4,390,406 A * | 6/1983 | Kato | G01N 27/301 |
| | | | 204/435 |
| 4,431,508 A | 2/1984 | Brown, Jr. et al. | |
| 4,454,007 A * | 6/1984 | Pace | G01N 27/3335 |
| | | | 204/403.06 |
| 5,180,481 A | 1/1993 | Carey | |
| 5,286,365 A | 2/1994 | Shu | |
| 5,840,168 A | 11/1998 | Chaniotakis et al. | |
| 2002/0038762 A1 | 4/2002 | Eventov et al. | |

OTHER PUBLICATIONS

Official Action dated Jun. 1, 2017, from corresponding Chinese Application No. 201480024943.6 along with an English translation.

* cited by examiner

LOW DRIFT ION SELECTIVE ELECTRODE SENSORS

TECHNICAL FIELD

This disclosure relates to ion selective electrodes and methods for making the same.

BACKGROUND

The ability to rapidly detect and analyze the concentration of a variety of ionic species or analytes in solution is helpful in many settings, for example, in the clinical, analytical or industrial chemical laboratory, or in large scale industrial or municipal applications such as water and wastewater treatment. Conventionally, in such analyses, an ion selective electrode (ISE) is brought into contact with a test solution into which a reference electrode is also immersed. The ion selective electrode and the reference electrode are connected via a voltmeter and a potentiometric determination of the activity of a particular analyte in solution is made. The activity measurement may be correlated to the concentration of the analyte in solution using reference solutions or standard solutions of known concentration.

Ion-selective ionophores are known, such as ionophores for ammonium, nitrate, nitrite lithium, sodium, potassium and calcium ions. It is known that for ISE electrode stability an internal electrochemical reference is needed. U.S. Pat. No. 4,431,508 discloses that a solid state ISE probe with a sylonized graphite rod reduces the drift of the probe. U.S. Pat. No. 4,214,968, U.S. Pat. No. 5,286,365 and U.S. Pat. No. 5,840,168 disclose that using an internal electrochemical reference element, usually as a Metal/Metal Salt composition in equimolar concentration, increases the stability of the ISE signal. However, known ion selective electrode sensors continue to suffer from problems with ISE signal drift and often involve very complicated production of compositions for the internal electrochemical reference. A solid state ISE with an internal electrochemical reference element causes the signal to drift over time in an unpredictable fashion that makes compensation difficult.

SUMMARY

We provide an ion selective electrode sensor including a housing containing an internal solution and enclosing a reference element containing a metal salt solution; at least one open mesh fabric sieve traversing an opening in the housing; and at least one ion sensitive film layer on the at least one mesh fabric sieve.

We further provide a method of making an ion selective electrode sensor including providing a housing having a proximal end portion and a distal end portion and assembling at least one woven mesh fabric sieve with at least one ion sensitive films on at least one surface of each sieve with the housing. We further provide a method of assembling a reference element including immersing an internal reference electrode comprised of Ag/AgCl wire in a tube with KCl solution and providing the tube with a porous frit.

DETAILED DESCRIPTION

Figure 1:
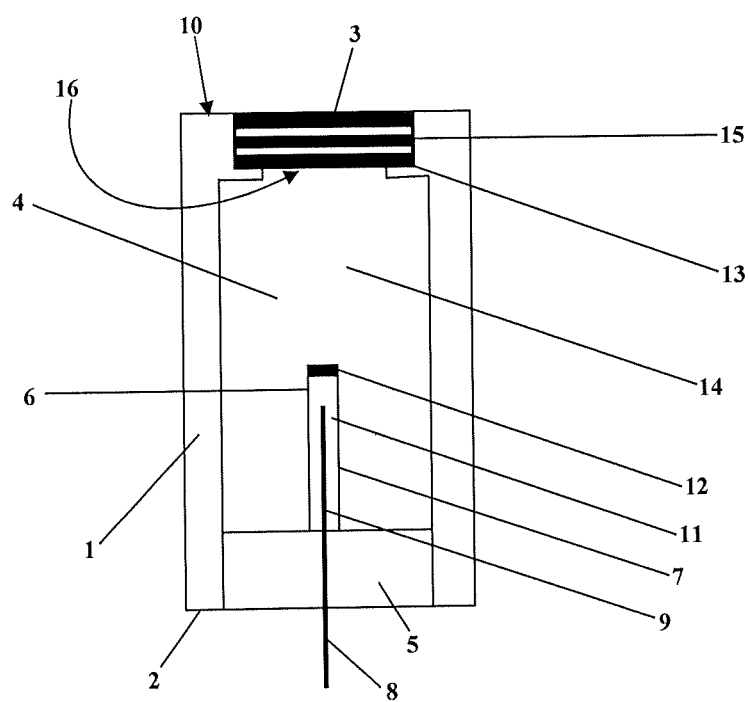
FIG. 1 is a schematic cross-sectional view of one example of an ion selective electrode sensor.

It will be appreciated that the following description is intended to refer to specific examples of a structure selected for illustration in the drawings and is not intended to define or limit the disclosure, other than in the appended claims.

FIG. 1 shows a representative example of an ion selective electrode sensor. The ion selective electrode sensor is generally referred to by the numeral 10. The ion selective electrode sensor 10 provides for detecting and measuring ions in fluids.

Referring to FIG. 1, an example of an ion selective electrode sensor 10 is illustrated by longitudinal cross-section. The ion selective electrode sensor 10 comprises a housing 1 having a proximal end portion 2 and a detection end portion 3. The housing 1 may be in the shape of a cylindrical tube having a hollow space 4 extending therethrough, although other shapes may be employed. The diameter of the hollow space 4 is preferably about ½ inch to about ¼ inch, but may be more or less. Different shapes or dimensions that do not alter functionability of the ion selective electrode sensor 10 may also be used. Use of the term "diameter" in reference to the housing 1 or other components should not be construed as limiting the structure of the ion selective electrode sensor as having a circular cross section. The housing 1 can have a cross-section of any shape or dimension.

As shown in FIG. 1, the housing has an opening 16, preferably provided on or near the detection end portion 3 of the housing 1. The opening 16 extends through a wall of the housing 1 to provide a pass through.

The housing 1 preferably may be formed from an electrically isolative material, including plastic type materials and the like. An exemplary material for forming the housing is polyvinyl chloride (PVC).

When the ion selective electrode sensor 10 is assembled, the housing 1 contains an internal solution 14 in the hollow space 4 of housing 1. Exemplary internal solutions 14 include electrolytes such as $KNO_3$, $NH_4Cl$, $NH_4NO_3$ or the like. Exemplary internal solutions 14 include 0.01M $NH_4Cl$ or 0.01 M $KNO_3$.

As shown in FIG. 1, the housing 1 may be provided with a base member 5 at the proximal end portion 2. The base member 5 may be made of an electrically isolative material, such as PVC or the like. The base member 5 preferably is configured to be received in the housing 1 at the proximal end 2. Preferably, base member 5 and housing 1 form an electrically isolative and liquid-tight junction at the proximal end portion 2 of the housing 1 when the base member 5 and housing 1 are assembled. Additionally, while base member 5 may be assembled with the housing 1, it is possible for the housing 1 and base member 5 to be formed with one-piece construction.

The base member 5 may be assembled with an internal reference element 6 extending within the hollow space 4 of the housing 1 toward the detection end portion 3. The reference element 6 may be a liquid junction internal electrochemical reference element. The reference element 6 may comprise a tube 7 having a size and shape receivable within the housing 1. Tube 7 may be formed from an electronically isolative material such as PVC, PVC-Tygon or the like, and contains a reference element solution 11. The reference element solution 11 may be a metal salt solution, for example, a solution of KCl and AgCl.

The reference element is provided with a porous frit 12. The porous frit 12 is provided separating the internal solution 14 and the reference element solution 11. For example, the porous frit 2 may be provided traversing an open end of tube 7 opposite of the base 5. The porous frit 12 is preferably made of a porous material, such as HDPE or PVC or the like. A suitable pore size of the porous frit includes pore sizes up to 100 microns, although pore size can be larger. Preferred pore sizes include up to 50 microns, such as 15 to 40 microns. The porous fit 12 provides for electrochemical communication between the reference element solution 11 in tube 7 and the internal solution 14.

A suitable porous frit may be a High Density Polyethylene (HDPE) rod purchased form Interstate Specialty Products (e.g., ROD-5520). The porous frit may have a diameter ranging up to 0.5 inches or more, preferably up to 0.25 inches, and be cut to a length of up to 10 mm or more, preferably 5 mm or more. ROD-5520 sold by Interstate Specialty Products has a diameter of 0.124 inches and may be cut to a length of 5 mm.

The reference element 6 further comprises an internal element 9 assembled in the tube 7 and immersed in the reference element solution 11. The internal element 9 may be formed from a metal and metal salt wire such as a Ag/AgCl wire or the like.

An electrical contact 8, preferably made from a conductive metal, such as silver or the like, may be assembled extending through base member 5. The electrical contact 8 preferably is assembled with the housing to be electrically connected with internal element 9 of the internal reference element 6 and extend externally of the housing 1. Additionally, the electrical contact 8 can be connected to a measurement device (not shown) in a known manner. The measurement device may be further attached to a display device (not shown). Alternatively, the electrical contact 8 may be attached to a single device that has both measurement and display functions.

As shown in FIG. 1, a sieve disk 13 is provided on or near the detection end 3 of the housing traversing or lying across at least part of the opening 16 in the housing 1. The sieve disk 13 supports at least one ISE film layer 15 while still allowing ion exchange to occur between a test solution outside of the housing 1 and the internal solution 14. A sieve disk 13 may be provided with at least one ISE film layer 15 on either or both the inner and outer facing surfaces of the sieve disk 13.

Figure 2:
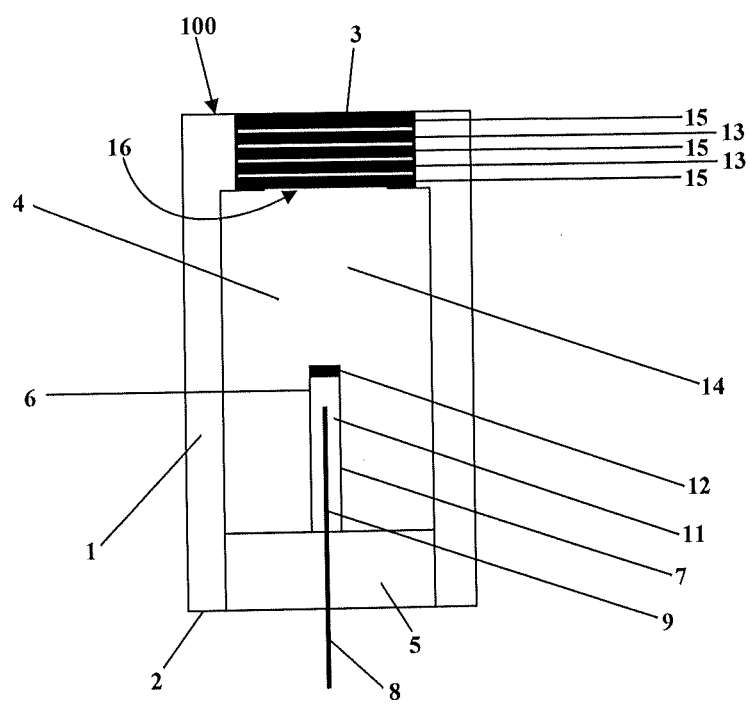
FIG. 2 is a schematic cross-sectional view of a further example of an ion selective electrode sensor.

FIG. 2 shows an alternative example of a sensor having two sieve disks 13 stacked together and provided on or near the detection end 3 of ion selective electrode sensor 100. As shown in FIG. 2, the ion selective electrode sensor 100 also comprises three ISE film layers 15. A first ISE film layer 15 is positioned on the sieve disk 13 closest to the proximal end portion 2 on a side of the sieve facing the hollow space 4 of the housing 1. A second ISE film layer 15 positioned between the two sieve disks 13. A third ISE film layer 15 is positioned on the sieve disk 13 farthest from the proximal end portion 2 on a side of the sieve disk 13 facing away from the hollow space 4 of the housing 1.

It will be appreciated that an ion selective electrode sensor can be provided with one, two or more sieve disks 13. Likewise, an ion selective electrode sensor can be provided with one, two, three or more ISE film layers 15.

The at least one sieve disk 13 may be a woven open mesh fabric such as a precision woven open mesh fabric manufactured by Sefar Inc. Preferably, the woven open mesh fabric of sieve disk 13 is constructed from polyester or polyamide (such as Nylon) fabric with a mesh size in the range of about 80 to 120 μm, preferably about 100 μm such as Sefar 07-100/32 fabric. The specific material type and size can be varied without changing the functionability of the sieve disk 13.

Preferably the at least one sieve 13 is affixed to the housing 1 traversing the opening 16. The sieve disk 13 may be affixed to the housing 1 or sealed at an external perimeter to the housing 1 by a gum or adhesive, for example. Preferably, the gum is comprised of PVC crumbs dissolved in cyclohexanone, but it can be any substance that adheres the sieve disks 13 to the housing 1 without interfering with the measurement. The gum adhesive may be allowed to dry/cure over the course of several hours or as long as needed to solidify and secure the sieve disks 13 in place.

At least one ISE film 15 is assembled with the at least one sieve disk 13 at the detection end portion 3 of housing 1. The ISE film 15 may also be provided in layers such as two, three or more layered ISE films. An ISE film 15 is assembled on the ion selective electrode sensor 10 such that it can electrochemically communicate between a test solution and the internal solution 14 in housing 1. An ISE film 15 can be disposed on either surface or both surfaces of the at least one sieve disk 13.

The ISE film 15 may be formed from an ionophore gel. The specific ionophore gel used may depend on the specific ion species the probe is being built to measure. We provide ion selective electrode sensors suitable to measure calcium ions, hydrogen ions, sodium ions, potassium ions, magnesium ions, nitrate ions, ammonia ions and the like.

Suitable ionophores include ETH 101 for measuring calcium ions, Tri-n-dodecylamin for measuring hydrogen ions, ETH 227 for measuring sodium ions, Valinomycin for measuring potassium ions and ETH 5506 or ETH 7025 for measuring magnesium ions, all of which can be purchased from Sigma-Aldrich. Other ionophores may also be used.

In an example of an ion selective electrode sensor made to detect and measure nitrate, the ionophore gel may comprise a nitrate ionophore. Nitrate ionophore gel can be purchased from Sigma-Aldrich or can be prepared by dissolving any type of Nitrate ionophore. Suitable nitrate ionophores include, but are not limited to, Tetraoctylammonium Nitrate, Tetradodecylammonium Nitrate, Tridodecylmethylammonium Nitrate, Tetraoctyl ammonium Bromide, Tetraoctadecylammonium Bromide or the like.

Nitrate ionophore gel may be prepared by using Tetraoctylammonium Bromide (TOABr) from Sigma-Aldrich (Product #87994), Five (5) mg of TOABr, 50 mg of PVC powder, and 200 mg 2-Nitrophenyloctyl ether may be placed in a 2 ml glass vial then 1 mL of THF is added to the vial. The contents of the vial may be shaken vigorously such as by using a Vortex-Genie (manufactured by Fisher Scientific), until the gel becomes clear.

When the ion selective electrode sensor is made to detect and measure ammonium, the ionophore gel may comprise an ammonium ionophore. Ammonium ionophore gel can be purchased from Sigma-Aldrich or can be prepared by dissolving an ammonium ionophore, such as Nonactin, in a solvent, such as THF. Ammonium ionophore gel may be made using about 2 mg of Nonactin (supplied by Promiliad Biopharma Inc.), about 14 mg of PVC powder, and about 70 mg of a plasticizer, such as bis(2-ethylhexyl) sebacate, combined in a 2 mL glass vial and about 0.4 mL of THF may be added to the mixture. The contents of the vial may be shaken vigorously such as by using a Vortex-Genie (manufactured by Fisher Scientific), until the gel becomes clear.

In addition to the use of bis(2-ethylhexyl) sebacate as a plasticizer, different plasticizers having different lipophilicity ability may also be used as an alternative or in combination. Suitable plasticizers include, but are not limited to, dibutyl phthalate (DBP), nitrophenyl octyl ester (NPOE), Tris(2-ethylhexyl) phosphate (TOP), Bis(1-butylpentyl) adipate (BBPA), and others known in the art.

Once an ionophore gel has been obtained or made, at least one ion sensitive film layer 15 may be made by pouring about 30 μl of ionophore gel by pipette onto a surface of a sieve 13. A second layer of 30 μl of ionophore gel may be added to the first ion sensitive film layer 15 after about 15-30 minutes. After another about 15-30 minutes, a third layer may be made by spreading about 30 μL of the ionophore gel on the previous ion sensitive film layer 15.

The amount of ionophore gel added to form each ion sensitive film layer 15 can be adjusted as needed. For example, the amount of PVC gel may be adjusted depending on the surface area of the sieve disk 13 to ensure full coverage and sufficient thickness of the at least one ion sensitive film layer 15.

An ion selective electrode sensor 10 may be manufactured by providing a housing 1 such as a PVC tube. Precision woven mesh fabric sieves 13 may be provided with ion sensitive film 15 applied to one or both of surfaces of the sieves 13. The sieves 13 may be affixed to an opening 16 at a detection end portion 3 of the housing 1 with the ion sensitive film 15 facing exteriorly of the housing 1. An internal solution 14 comprising 0.01M $NH_4Cl$ or 0.01M $KNO_3$ or 0.01M $NH_4NO_3$ may be introduced within the housing 1 such that internal solution 14 has contact with the sieve 13.

An internal reference element 6 may be assembled by providing a PVC tube 7 of a size and shape receivable in the housing 1. An Ag/AgCl wire 9 can be inserted into one end of the PVC tube 7 and a porous PVC fit 12 may be inserted into the other end of the tube 7. A 3.8M KCl solution saturated with AgCl may be introduced into the tube 7 and the assembled reference element 6 may be mounted to a base member 5. The base member 5 may be fixed to the proximal end 2 of the housing 1 with the internal reference element 6 directed towards the interior of the housing 1.

The subject matter of all cited patents, published patent applications and references are incorporated by reference.

Although specific examples have been shown and described herein for purposes of illustration and exemplification, it is understood that the specific examples shown and described may be substituted for a wide variety of alternative and/or equivalent implementations without departing from the scope of this disclosure. This disclosure is intended to cover any adaptations or variations of the examples discussed herein.

What is claimed is:

1. An ion selective electrode sensor comprising;
   a housing containing an internal solution and enclosing a reference element containing a metal salt solution;
   at least one open mesh fabric sieve traversing an opening in the housing; and
   at least three ion sensitive film layers on the at least one open mesh fabric sieve.

2. The ion selective electrode sensor of claim 1, wherein the ion sensitive film layers are an ionophore gel.

3. The ion selective electrode sensor of claim 2, wherein the ionophore gel comprises at least one nitrate ionophore selected from the group consisting of tetraoctylammonium nitrate, tetradodecylammonium nitrate, tridodecylmethylammonium nitrate, tetraoctyl ammonium bromide, and tetraoctadecylammonium bromide.

4. The ion selective electrode sensor of claim 3, wherein the nitrate ionophore is tetraoctyl ammonium bromide.

5. The ion selective electrode sensor of claim 1, wherein the at least one open mesh fabric sieve is formed from polyester.

6. The ion selective electrode sensor of claim 1, wherein the at least one open mesh fabric sieve is formed from nylon.

7. The ion selective electrode sensor of claim 1, wherein the at least one open mesh fabric sieve has a mesh size of between 80 μm and 120 μm.

8. The ion selective electrode sensor of claim 1, wherein the reference element is a liquid junction internal electrochemical reference element comprising an Ag/AgCl wire.

9. The ion selective electrode sensor of claim 1, wherein the metal salt solution in the reference element is a solution of AgCl or KCl.

10. The ion selective electrode sensor of claim 1, wherein the reference element comprises a porous frit.

11. The ion selective electrode sensor of claim 10, wherein the porous frit separates the internal solution and metal salt solution.

12. A method of making an ion selective electrode sensor comprising:
    providing a housing having a proximal end portion and a distal end portion;
    positioning at least one open mesh fabric sieve disk to traverse an opening of the housing;
    forming a first ion sensitive film layer on the at least one sieve disk,
    forming a second ion sensitive film layer on the first ion sensitive film layer, and
    forming a third ion sensitive film layer on the second ion sensitive film layer.

13. An ion selective electrode sensor comprising:
    a housing containing an internal solution and enclosing a reference element containing a metal salt solution;
    at least one open mesh fabric sieve traversing an opening in the housing;
    a first ion sensitive film layer on the open mesh fabric sieve; and
    a second ion sensitive film layer applied to the first ion sensitive film layer.

14. The ion selective electrode sensor of claim 13, further comprising a third ion sensitive film layer applied to the second ion sensitive film layer.

15. An ion selective electrode sensor comprising;
    a housing containing an internal solution and enclosing a reference element containing a metal salt solution;
    at least two or more open mesh fabric sieves traversing an opening in the housing; and
    at least one ion sensitive film layer on at least one of the open mesh fabric sieves.

* * * * *